US00PP36023P2

(12) United States Plant Patent
Meilland

(10) Patent No.: US PP36,023 P2
(45) Date of Patent: Jul. 23, 2024

(54) MINIATURE ROSE PLANT NAMED 'MEIHELIOT'

(50) Latin Name: *Rosa hybrida*
Varietal Denomination: MEIHELIOT

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 17 days.

(21) Appl. No.: 18/233,011

(22) Filed: Aug. 11, 2023

(51) Int. Cl.
*A01H 5/02* (2018.01)
*A01H 6/74* (2018.01)

(52) U.S. Cl.
USPC ..... Plt./128

(58) Field of Classification Search
USPC ..... Plt./101, 123, 128
See application file for complete search history.

(56) References Cited

U.S. PATENT DOCUMENTS

| | | | |
|---|---|---|---|
| PP9,652 | P | 10/1996 | Meilland |
| PP9,973 | P | 7/1997 | Meilland |
| PP16,202 | P2 | 1/2006 | Radler |

*Primary Examiner* — Susan McCormick Ewoldt
*Assistant Examiner* — Zachariah Allan Kay
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'MEIHELIOT', is disclosed. The new variety forms double, hot pink colored flowers. Dense, semi-glossy foliage is formed, which contrasts with the blossoms. A bushy growth habit is displayed. The new variety is well suited for providing attractive ornamentation in the landscape.

1 Drawing Sheet

Latin name of genus and species of plant claimed: *Rosa hybrida.*

Variety denomination: 'MEIHELIOT'.

STATEMENT REGARDING PRIOR DISCLOSURES BY THE INVENTOR

The first offer for sale of the new variety was Oct. 7, 2022, in the United States of America. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was the 'MEIKANROU' variety (U.S. Plant Pat. No. 9,973). The male parent (i.e., the pollen parent) was an unnamed seedling (not patented) which is the product of a cross between an unnamed seedling (not patented) and the 'RADTKO' variety (U.S. Plant Pat. No. 16,202).

The parentage of the new variety can be summarized as follows:

'MEIKANROU' X (Unnamed Seedling X 'RADTKO')

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, semi-hardwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms bright hot pink colored flowers,
(b) produces double flowers, and
(c) exhibits a bushy growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'MEIKANROU' variety (i.e., the seed parent) provides dark red colored flowers with typically between 65 to 85 petals, whereas the new variety provides hot pink colored flowers with typically between 40 to 50 petals. In addition, the unnamed seedling male parent (i.e., pollen parent) display flowers which are smaller and produce less petals compared to flowers of the new variety. Moreover, the new variety can be readily distinguished from other similar non-parental varieties. For example, the 'MEIFERJAC' variety (U.S. Plant Pat. No. 9,652) provides stable red colored flowers with approximately 27 petals on average, whereas the new variety provides hot pink colored flowers with typically between 40 to 50 petals.

The new variety has been named 'MEIHELIOT'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately nine months of age and were observed during May while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms and The R.H.S. Colour Chart designation used herein represents the closest color observed on the majority of the specified botanical feature. The description is based on the observation of nine-months-old specimens of the new variety during May while budded on their own roots and growing outdoors at Le Cannet des Maures, Var, France.

Botanical classification: *Rosa hybrida* cultivar MEIHELIOT.

Commercial classification: Miniature Rose Plant.

Plant:

*Habit.*—Bushy.

*Height.*—Approximately 40 cm on average.

*Width.*—Approximately 40 cm on average.

Branches:

*Color.*—Young stems: a color between Green Group 141A and Yellow-Green Group 146A. — adult wood: Green Group 143A.

*Length.*—Fom the crown to the flower is approximately 30 cm on average.

*Diameter.*—Approximately 0.3 cm on average.

*Prickles.*—Configuration on adult stems: slightly concave, very elongated on the upper surface and very concave on the under surface. — long prickles — quantity: typically between 3 to 5 prickles per 10 cm long young stem and typically between 10 to 15 prickles per 10 cm long adult stem. — long prickles — length: typically between 0.3 cm to 0.5 cm on young stems and on adult stems. — long prickles — width at base: approximately 0.1 cm on average on young stems and approximately 0.2 cm on average on adult stems. — long prickles — base shape: obovate, very narrow, and short on young stems; oval, narrow, and short on adult stems. — long prickles — color on young stems: Greyed-Orange Group 165C more or less suffused with Greyed-Red Group 179B. — long prickles — color on adult stems: Greyed-Orange Group 165A. — small prickles: absent.

*Internode.*—Numbers on the entire branch: typically between 3 to 5. — length: approximately 1.5 cm on average.

Foliage:

*General appearance.*—Dense, semi-glossy.

*Number of leaflets.*—3, 5, 7; most often 7.

7 *leaflets leaf.*—Length: typically between 8.5 cm to 12.5 cm. — width: typically between 5.0 cm to 7.0 cm.

*Terminal leaflet.*—Length: typically between 3.4 cm to 5.0 cm. — width: typically between 1.5 cm to 2.5 cm.

*Young shoots.*—Anthocyanin coloration: Greyed-Purple Group 183C.

*New foliage.*—Upper surface color. Green Group 139A. — under surface color. Green Group 137B.

*Adult foliage.*—Upper surface color. Green Group 139A. — under surface color. Green Group 137B.

Leaflets:

*Shape.*—Tip: acuminate. — base: obtuse.

*Intensity of glossiness.*—Medium.

*Texture.*—Moderately leathery.

*Smoothness.*—Upper surface is smooth and under surface is bumpy.

*General appearance.*—Elliptical.

*Serration.*—Small and single.

*Undulation on the margin.*—Very weak.

*Venation.*—Color is a color between Yellow-Green Group 144A and 144B; and pattern is imparipinnate.

*Petiole rachis.*—Color of upper surface: Green Group 137A on the edge and Greyed-Red Group 179A on the center. — color of under surface: a color between Yellow-Green Group 144A and 144B. — texture: upper surface is glandular, under surface is little prickles. — rachis of terminal leaflet: length is typically between 3.5 cm to 4.5 cm and diameter is approximately 0.1 cm on average.

*Petioles.*—Upper surface: glandular. — under surface: little prickles. — color of upper surface: Green Group 137A on the edge and Greyed-Red Group 179B on the center. — color of under surface: a color between Yellow-Green Group 144A and 144B. — length: typically between 1.5 cm to 3.0 cm. — diameter approximately 0.1 cm on average.

*Stipules.*—Length: approximately 1.5 cm on average. — width: approximately 0.5 cm on average. — general appearance: broad. — texture: smooth on upper and under surfaces. — color of upper surface: Yellow-Green Group 144A more or less suffused with Green Group 137A. — color of under surface: Yellow-Green Group 144A more or less suffused with Green Group 137A.

Inflorescence:

*Number of flowers per stem.*—Tupically between 2 to 5 flowers per stem.

*Lastingness of the bloom.*—On the plant: approximately 15 days on average. — in vase: not tested.

*Bud.*—Shape: elongated. — size: small. — length: approximately 2.0 cm on average. — width: approximately 1.5 cm on average. — color as calyx breaks: upper surface: a color between Red- Purple Group 57A and Red Group 53C; basal spot is very little and color is Yellow Group 3C. under surface: Red-Purple Group 57A; basal spot is very little and color is Yellow Group 3C.

*Sepals.*—Number commonly 5. — length: typically between 2.0 cm to 2.5 cm. — width: approximately 0.7 cm. — shape: at the top: elongated and narrow. at the base: flat at union with the receptacle. — extensions: absent. — upper surface: texture: tomentous. color: Yellow-Green Group 144A suffused with Green Group 143A and covered with little hairs Green-White Group 157B. — under surface: texture: smooth and glandular on the edge. color Yellow-Green Group 144A suffused with Green Group 143A.

*Receptacle.*—Color. Yellow-Green Group 144A. — length: typically between 0.5 cm to 1.0 cm. — width: approximately 0.5 cm on average. — surface: smooth. — shape: pitcher shaped.

*Peduncle.*—Length: approximately 5.5 cm on average. — width: approximately 0.2 cm on average. — surface: glandular. — color Yellow-Green Group 144A.

*Flower.*—Diameter when open: typically between 4.5 cm to 6.0 cm. — depth of the flower: approximately 1.5 cm on average. — shape: flat cup shaped. — shape when viewed from above: irregular rounded. — shape of the upper part of the flower profile: flattened convex. — shape of the lower part of the flower profile: flat. — type: double. — number of petals under normal conditions: typically between 40 to 50. — petals: general shape: external petals are rounded and internal petals are obovate. shape at the base: acute. shape at the top: rounded. texture: semi-hard. length: external petals are typically between 2.0 cm to 2.5 cm; internal petals are approximately 1.5 cm on average. width: external petals are typically between 2.0 cm to 2.5 cm; internal petals are approximately 1.0 cm on average. — undulation of the petal: weak. — reflexing of the petal: only external petals — very weak. — petal incision: absent. — petal arrangement: imbricated with petaloids (very little petals deformed as anthers). — petal drop: petals drop off cleanly before drying. — fragrance: none. — discoloration of the flower: no. — color when opening: basal spot on the upper surface: Yellow Group 3D. upper surface: Red-Purple Group 57A. basal spot on the under surface: Yellow Group 3D. under surface: Red-Purple Group 57B. — color of the open flower: basal spot on upper surface: White Group 155C. upper surface: Red-Purple Group 57B. basal spot on under surface: White Group 155C. under surface of the flower: Red-Purple Group 57C. — anthers: approximately 50 on average, length is approximately 0.2 cm on average, width is approximately 0.1 cm on average, coloration is Yellow-Orange Group 21A, and arrangement is regular around styles. — filaments: length is approximately 0.3 cm on average and coloration is Yellow Group 3C at the base and transitions to Orange-Red Group 33C. — styles: length is approximately 0.5 cm, coloration is Red Group 53A, and number is approximately 60 on average. — stigmas: length is approximately 0.1 cm on average and coloration is Yellow Group 6B. — pollen: medium quantity; color is Yellow-Orange Group 15A. — hips: information not available; very few produced.

Development:

*Vegetation.*—Strong.

*Blooming.*—Early in the season abundant and nearly continuous, typically from May to first frost in France.

*USDA hardiness zone.*—Test to Zone 5.

*Tolerance to disease.*—Good, and particularly against powdery mildew (*Podosphaera pannosa*) and rust (*Phragmidium* sp).

The new 'MEIHELIOT' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIHELIOT' characterized by the following combination of characteristics:

(a) forms bright hot pink colored flowers, (b) produces double flowers, and (c) exhibits a bushy growth habit;

substantially as herein shown and described.

* * * * *

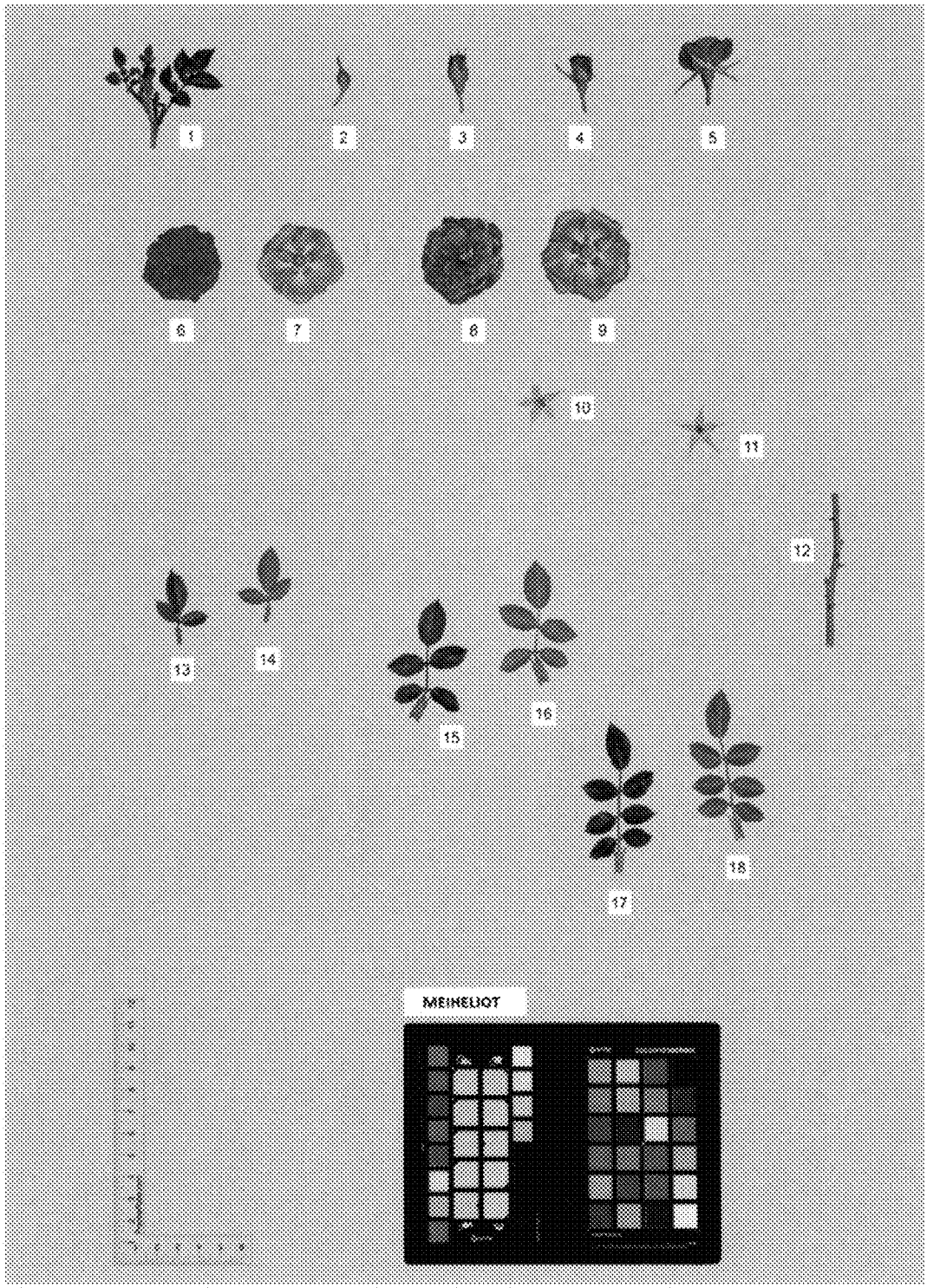
1
2
3
4
5
6
7
8
9
10
11
12
13
14
15
16
17
18
MEINELIOT